(12) United States Patent
Ando et al.

(10) Patent No.: US 9,566,044 B2
(45) Date of Patent: Feb. 14, 2017

(54) MEDICAL IMAGE DISPLAY APPARATUS AND ULTRASONIC DIAGNOSIS APPARATUS

(75) Inventors: Kouji Ando, Otawara (JP); Shouichi Nakauchi, Nasushiobara (JP); Takeshi Sugio, Otawara (JP); Takashi Masuda, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 718 days.

(21) Appl. No.: 12/958,806

(22) Filed: Dec. 2, 2010

(65) Prior Publication Data

US 2011/0144498 A1 Jun. 16, 2011

(30) Foreign Application Priority Data

Dec. 11, 2009 (JP) ................. 2009-282037

(51) Int. Cl.
*A61B 8/00* (2006.01)
*A61B 8/08* (2006.01)
*G06T 19/00* (2011.01)

(52) U.S. Cl.
CPC .............. *A61B 8/466* (2013.01); *A61B 8/463* (2013.01); *A61B 8/469* (2013.01); *A61B 8/483* (2013.01); *G06T 19/003* (2013.01); *G06T 2210/41* (2013.01); *G06T 2219/004* (2013.01); *G06T 2219/028* (2013.01)

(58) Field of Classification Search
CPC ......... A61B 8/466; A61B 8/461; A61B 8/469; G06T 2219/028; G06T 2210/41; G06T 2219/004

See application file for complete search history.

(56) References Cited

U.S. PATENT DOCUMENTS

| 4,624,007 A | * | 11/1986 | Muranushi | ......................... 378/4 |
| 6,925,200 B2 | * | 8/2005 | Wood et al. | .................. 382/132 |
| 2002/0070970 A1 | * | 6/2002 | Wood et al. | .................. 345/766 |
| 2004/0138559 A1 | * | 7/2004 | Cheng et al. | ................. 600/437 |

FOREIGN PATENT DOCUMENTS

| JP | 2001-37756 A | 2/2001 |
| JP | 2005-169070 A | 6/2005 |
| JP | 2011-36474 A | 2/2011 |

OTHER PUBLICATIONS

Office Action issued Sep. 17, 2013, in Japanese Patent Application No. 2009-282037 with English translation.

* cited by examiner

*Primary Examiner* — Amanda Lauritzen Moher
(74) *Attorney, Agent, or Firm* — Oblon, McClelland, Maier & Neustadt, L.L.P.

(57) ABSTRACT

According to one embodiment, a medical image display apparatus includes a storage unit storing data of a three-dimensional image, a slice image generating unit generating three slice images associated with three slices from the three-dimensional image, a display unit displaying the three slice images respectively in three display areas, an ROI marker generating unit generating three ROI markers to be respectively superimposed on the displayed three slice images, the three ROI markers corresponding to a single ROI, an operation unit performing operation of changing relative positions between the three slice images and the three ROI markers, and a display control unit controlling move the three slice images in the three display areas in accordance with the operation of changing the relative positions and fix the three ROI markers at center positions of the three display areas.

14 Claims, 5 Drawing Sheets

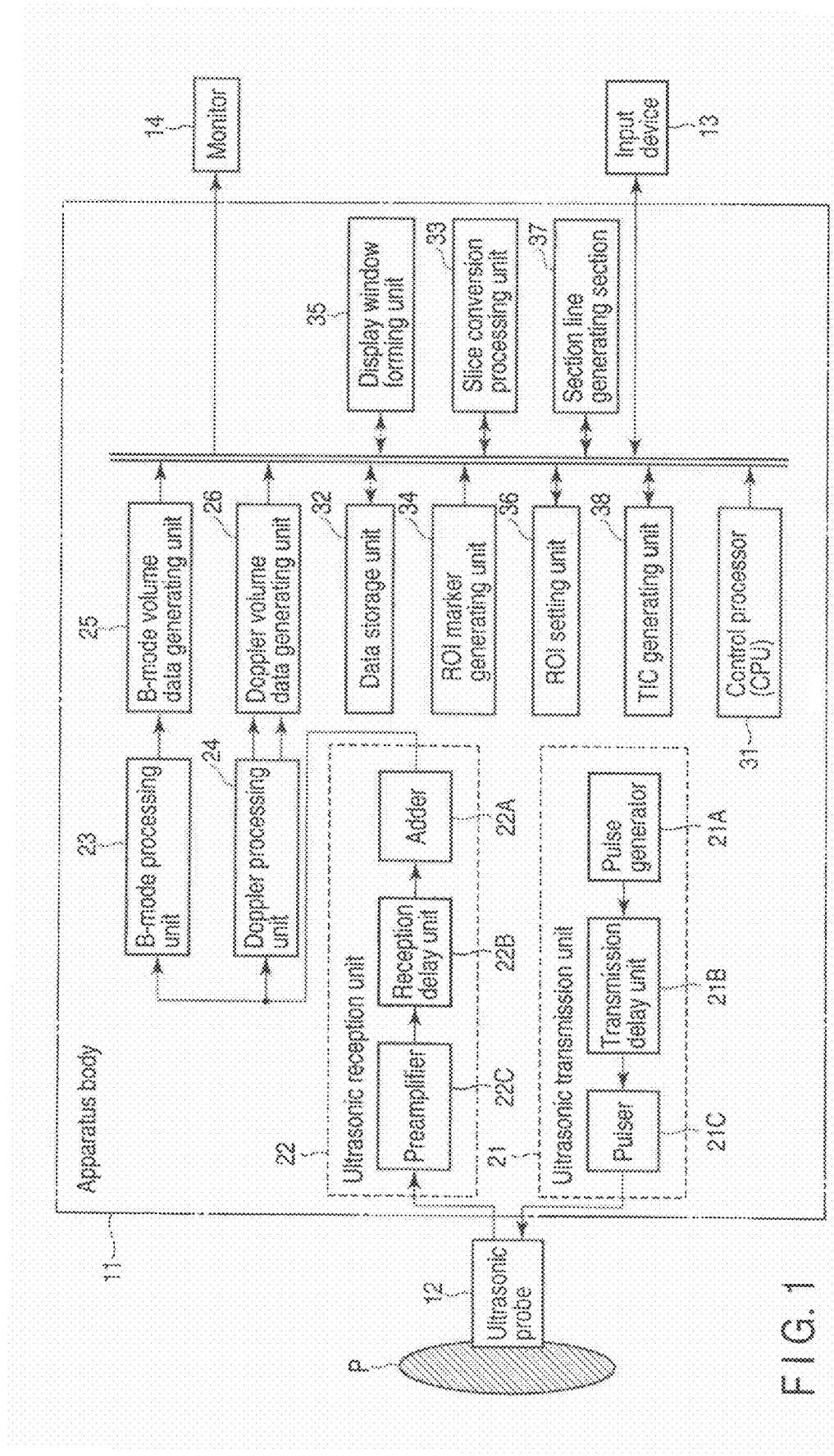
F I G. 1

MEDICAL IMAGE DISPLAY APPARATUS AND ULTRASONIC DIAGNOSIS APPARATUS

CROSS-REFERENCE TO RELATED APPLICATIONS

This application is based upon and claims the benefit of priority from Japanese Patent Application No. 2009-282037, filed Dec. 11, 2009; the entire contents of which are incorporated herein by reference.

FIELD

Embodiments described herein relate generally to an image display apparatus.

BACKGROUND

A time intensity curve is provided as an index effective for diagnosis, which represents a temporal change in the luminance value or luminance average of a region of interest set on a two-dimensional ultrasonic image. An operator sets a region of interest by moving, for example, a circular, quadrilateral, or polygonal ROI marker to the region of interest on a two-dimensional ultrasonic image with a mouse or trackball.

It is more difficult to align an ROI marker with a portion of interest on a three-dimensional ultrasonic image than on a two-dimensional ultrasonic image.

BRIEF DESCRIPTION OF THE DRAWING

FIG. 1 is a block diagram showing the arrangement of an ultrasonic diagnosis apparatus according to an embodiment;

DETAILED DESCRIPTION

Figure 2:
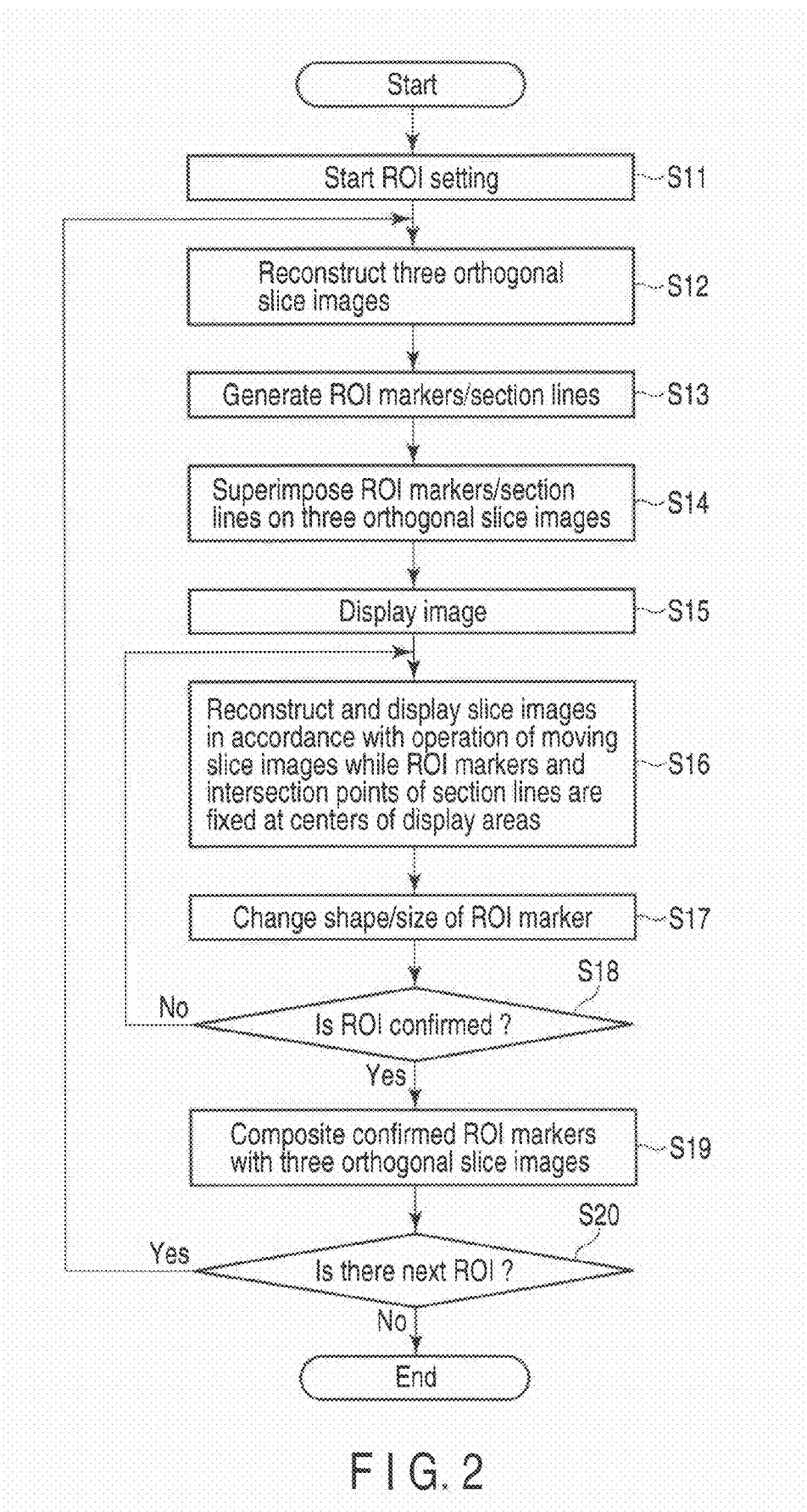
FIG. 2 is a flowchart showing a processing procedure for setting a plurality of ROI markers on a plurality of regions of interest according to this embodiment.

In general, according to one embodiment, a medical image display apparatus includes a storage unit configured to store data of a three-dimensional image associated with an object; a slice image generating unit configured to generate three slice images associated with three slices from the three-dimensional image; a display unit configured to display the three slice images respectively in three display areas; an ROI marker generating unit configured to generate three ROI markers to be respectively superimposed on the displayed three slice images, the three ROI markers corresponding to a single ROI; an operation unit configured to perform operation of changing relative positions between the three slice images and the three ROI markers; and a display control unit configured to control the slice image generating unit, the display unit, and the ROI marker generating unit so as to move the three slice images in the three display areas in accordance with the operation of changing the relative positions and fix the three ROI markers at center positions of the three display areas.

This embodiment will be described below with reference to the views of the accompanying drawing. A medical image display apparatus of the embodiment has as an objective a three-dimensional image associated with a three-dimensional region of an object. Medical image generating apparatuses capable of generating three-dimensional images typically include ultrasonic diagnosis apparatuses, X-ray computed tomographic apparatuses, and magnetic resonance imaging apparatuses. The medical image display apparatus according to the embodiment can be applied to any of ultrasonic diagnosis apparatuses, X-ray computed tomographic apparatuses, and magnetic resonance imaging apparatuses. In addition, the medical image display apparatus according to the embodiment is configured separately from a medical image generating apparatus or mounted on the medical image generating apparatus. The following description will be made on the assumption that the medical image display apparatus according to the embodiment is mounted on the ultrasonic diagnosis apparatus.

FIG. 1 shows the arrangement of an ultrasonic diagnosis apparatus according to this embodiment. This ultrasonic diagnosis apparatus includes an ultrasonic diagnosis apparatus body 11, an ultrasonic probe 12, an input device 13, and a monitor 14. The ultrasonic probe 12 includes a plurality of piezoelectric transducers. The plurality of piezoelectric transducers are arrayed in a two-dimensional matrix. This array allows three-dimensional electronic scanning. The plurality of piezoelectric transducers generate ultrasonic waves upon receiving driving signals from an ultrasonic transmission unit 21 of the apparatus body 11. The plurality of piezoelectric transducers convert reflected waves from an object into electrical signals. A matching layer is placed in front of the piezoelectric transducers. A backing layer for preventing the propagation of ultrasonic waves is placed on the rear surface of the piezoelectric transducers.

The ultrasonic waves transmitted from the ultrasonic probe 12 to an object P are sequentially reflected by the discontinuity surface of acoustic impedance of an internal body tissue. The ultrasonic probe 12 receives the reflected waves. The amplitude of an echo signal reflects an acoustic impedance difference on the discontinuity surface. The transmitted ultrasonic waves undergo a frequency shift due to the Doppler effect caused by a moving blood flow, cardiac wall, or the like.

The input device 13 is connected to the apparatus body 11 and includes various types of switches, buttons, a trackball, a mouse, and a keyboard which are used to input, to the apparatus body 11, various types of instructions, operation to set a region of interest (ROI), and the like from an operator. The monitor 14 a display unit for displaying ultrasonic images, a window to set a region of interest, and the like.

The apparatus body 11 includes the ultrasonic transmission unit 21, an ultrasonic reception unit 22, a B-mode processing unit 23, a Doppler processing unit 24, a B-mode volume data generating unit 25, and a Doppler volume data generating unit 26. The ultrasonic transmission unit 21 includes a pulse generator 21A, a transmission delay unit 21B, and a pulser 21C. The pulse generator 21A repeatedly generates rate pulses for the formation of transmission ultrasonic waves at a predetermined rate frequency fr Hz (period: 1/fr sec). The transmission delay unit 21B gives each rate pulse for each channel the delay time required to focus an ultrasonic wave into a beam for each channel and determine a transmission directivity in two directions (azimuth direction and elevation direction) for three-dimensional scanning. The pulse generator 21A applies a driving pulse to the probe 12 at the timing based on this rate pulse for each channel.

The ultrasonic reception unit 22 includes a preamplifier 22C, an A/D converter, a reception delay unit 22B, and an adder 22A. The preamplifier 22C amplifies an echo signal received via the ultrasonic probe 12 for each channel. The reception delay unit 22B gives each amplified echo signal the delay time required to determine a reception directivity in two directions (azimuth direction and elevation direction) for three-dimensional scanning. The adder 22A then performs addition processing for the resultant signals. With this addition, the reflection component of the echo signal from the direction corresponding to the reception directivity is enhanced, and a synthetic beam for ultrasonic transmission/reception is formed in accordance with the reception directivity and transmission directivity.

The B mode processing unit 23 receives the echo signal from the ultrasonic reception unit 22, and performs logarithmic amplification, envelope detection processing, and the like for the signal, thereby generating data whose signal strength is represented by a brightness level. The B-mode volume data generating unit 25 converts output data from the B-mode processing unit 23 into data expressed in the XYZ coordinate system, and performs interpolation processing to obtain a uniform resolution, as needed, thereby generating B-mode volume data.

The Doppler processing unit 24 frequency-analyzes velocity information from the echo signal received from the reception unit 22 to extract a blood flow, tissue, and contrast medium echo component by the Doppler effect, and obtains blood flow information such as an average velocity, variance, and power at multiple points. The Doppler volume data generating unit 26 converts the output data from the B-mode processing unit 23 into data expressed in the XYZ coordinate system, and performs interpolation processing to obtain a uniform resolution, as needed, thereby generating Doppler volume data. Note that three-dimensional ultrasonic image data is defined to represent B-mode volume data or Doppler volume data.

A data storage unit 32 is provided to store three-dimensional ultrasonic image data. A slice conversion processing unit 33 generates typically three slice images associated with three orthogonal slices designated by a control processor 31 from stored three-dimensional ultrasonic image data. Three slice images need not necessarily be associated with three orthogonal slices, and may be associated with three slices obliquely intersecting each other or three parallel slices.

Figure 3:
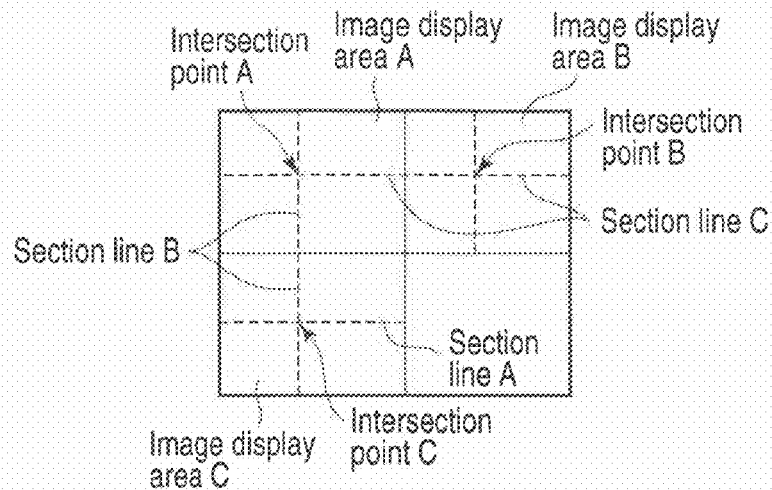
FIG. 3 is a view showing a display window example formed by a display window generating unit in FIG. 1.

A technique of generating a slice image from three-dimensional image data is known as MPR (Multi Planar Reconstruction). The monitor 14 displays the three slice images associated with three orthogonal slices which are generated by the slice conversion processing unit 33. A display window forming unit 35 forms a display window on the monitor 14. As shown in FIG. 3, the display window forming unit 35 divides the display window into three display areas A, B, and C. Three slice images associated with three orthogonal slices are arranged in the three display areas A, B, and C.

An ROI marker generating unit 34 generates ROI marker data corresponding to the positions, shapes, and sizes designated from the input device 13 under the control of the control processor 31. The display window forming unit 35 superimpose these ROI markers on the slice images arranged in the display areas A, B, and C. A section line generating section 37 generates the data of section lines A, B, and C representing the mutual positions of three slice images arranged in the three display areas A, B, and C. The display window forming unit 35 superimposes the section lines A, B, and C on the slice images arranged in the display areas A, B, and C. Two section lines superimposed on one slice image displayed in one of three display areas correspond to the slice positions of two slice images displayed in the two remaining display areas. Moving a given section line will update the slice images corresponding to the section line.

An ROI setting unit 36 sets a region of interest (ROI) in the range defined by the ROI marker confirmed via the input device 13. A TIC generating unit 38 generates a time intensity curve (TIC) based on pixel values in the set region of interest.

This embodiment is configured to reduce the load of the operation of aligning a plurality of ROI markers with a plurality of portions of interest in a three-dimensional ultrasonic image. Detailed operation for this processing will be described below. This operation is executed under the control of the control processor 31.

FIG. 2 shows a processing procedure for setting a plurality of ROI markers in a plurality of regions of interest according to this embodiment. The following will exemplify a case in which regions of interest are set at two portions of interest a and b by using two ROI markers including the first and second ROI markers.

Figure 4:
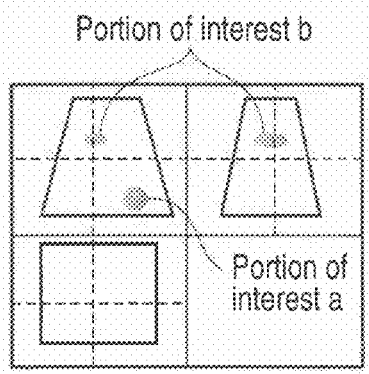
FIG. 4 is a view showing an initial window displayed on a monitor in FIG. 1.

The control processor 31 starts an ROI setting algorithm in accordance with an instruction to start setting an ROI which is issued via the input device 13 (S11). Initially, three slices are set to intersect at the center point of a three-dimensional region scanned with ultrasonic waves. Three slice images associated with three orthogonal slices designated by the control processor 31 are reconstructed from three-dimensional ultrasonic image data (S12). As shown in FIG. 4, the monitor 14 displays the reconstructed images.

Figure 5:
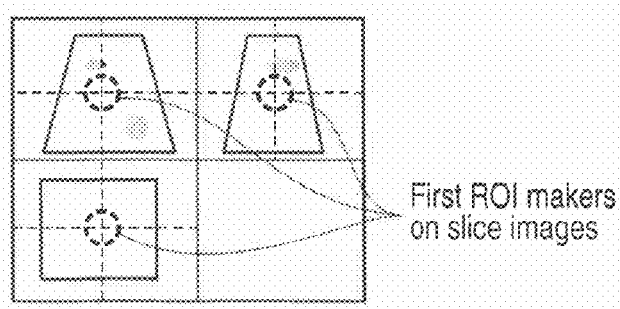
FIG. 5 is a view showing a window corresponding to step S15 in FIG. 2.

The ROI marker generating unit 34 generates three ROI markers corresponding to the three slice images, and the section line generating section 37 generates three section lines A, B, and C representing the mutual positions of the three slice images (S13). Obviously, the three ROI markers correspond to the same position on a three-dimensional coordinate form. The display window forming unit 35 superimposes three ROI markers and three section lines A, B, and C on the three slice images (S14), and displays the markers and section lines on the three slice images, as shown in FIG. 5 (S15). Note that it is possible to move the ROI markers superimposed on the slice images independently of them. Confirmed ROI markers (to be described later) are fixed at confirmed positions on slice images, and are moved together with the slice images.

Two section lines are arranged in each of the three display areas A, B, and C. These two section lines represent the positions of the two remaining slices. The intersection point of two section lines in each of the display areas A, B, and C is fixed to the center of a corresponding one of the three display areas A, B, and C. The centers of the three ROI markers are respectively fixed to the centers of the three display areas A, B, and C.

Figure 6:
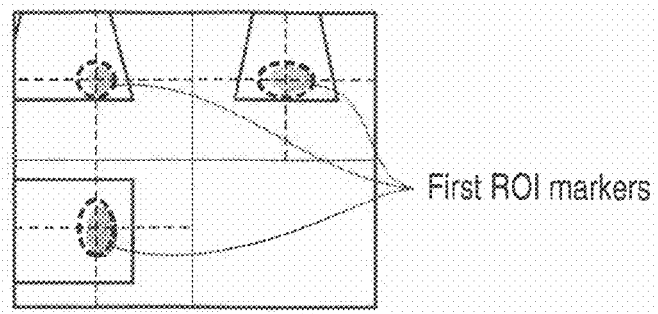
FIG. 6 is a view showing the first ROI markers corresponding to step S16 in FIG. 2.

While the centers of the ROI markers and the intersection points of the section lines are fixed to the centers of the display areas A, B, and C, the control processor 31 moves the slice images within the display areas A, B, and C in accordance with moving operation with the input device 13, typically dragging operation (S16). As shown in FIG. 6, the operator operates the input device 13 to move the slice images and adjust the shapes and sizes of the ROI markers so as to make the ROI markers include the portions of interest a (S17). When the ROI markers include the portions of interest a, the operator inputs an instruction to confirm (S18). This allows the ROI setting unit 36 to set ROIs including the portions of interest a.

The ROI marker generating unit 34 generates ROI markers (confirmed ROI markers) corresponding to the confirmed ROIs. A confirmed ROI marker is displayed in a form different from that of an ROI marker corresponding to an ROI which is not confirmed. For example, a confirmed ROI marker has a blue color, and an ROI marker which is not confirmed has a red color. The operator can discriminate a confirmed ROI marker from the next ROI marker during operation.

Each confirmed ROI marker is composited at a confirmed position on a slice image under the control of the control processor 31 (S19). The composited ROI marker is fixed relative to the slice image. When the operator performs the operation of moving the slice image, the ROI marker is moved on the display window, together with the slice image.

Figure 7:
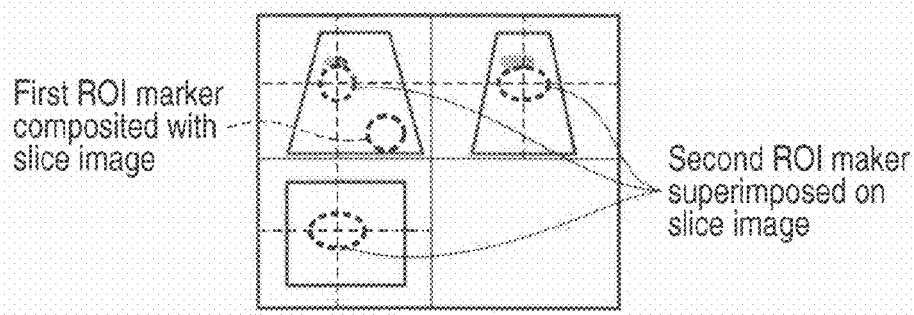
FIG. 7 is a view showing the first ROI marker corresponding to step S19 in FIG. 2.
Figure 8:
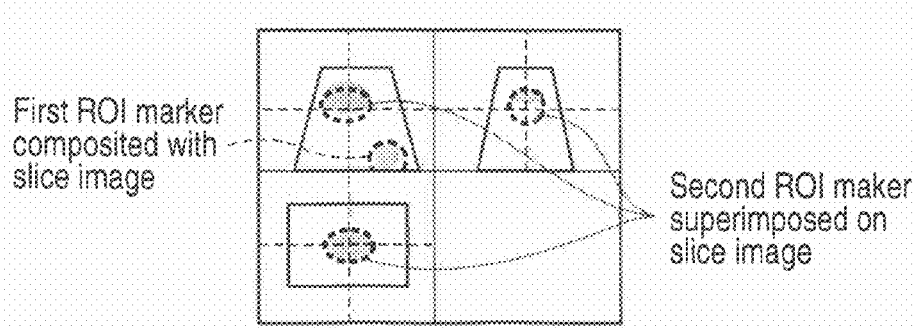
FIG. 8 is a view showing the confirmed first and second ROI markers corresponding to step S16 in FIG. 2.

If there is another region of interest to be set (S20), the process returns to step S12 to repeat the same processing as that in steps S12 to S19. As shown in FIGS. 7 and 8, the new second ROI marker is superimposed on the slice image. The confirmed first ROI marker is composited on the portion of interest a on the slice image, and is moved together with the slice image.

As described above, an ROI marker and the intersection point of section lines are fixed to the center of a display area, and the slice image is moved. The ROI marker is not lost on the slice image, and the ROI marker can be moved onto a portion of interest while being always captured at the center of the display area. In addition, since the confirmed ROI marker is displayed while being composited on the slice image, the operator can always refer to the ROI marker for the next ROI setting operation. This makes it possible to reduce the load of the operation of aligning a plurality of ROI markers with a plurality of portion of regions in a three-dimensional ultrasonic image.

Note that it is possible to display a confirmed ROI marker so as to allow to move the ROI marker on a slice image, together with the next ROI marker which is being set, independently of the slice image, while the position of the confirmed ROI marker relative to the next ROI marker is fixed, instead of fixing the confirmed ROI marker at a confirmed position on the slice image.

The operator can arbitrarily switch, by mode switching instruction operation, between the mode of fixing a confirmed ROI marker relative to a slice image and the mode of fixing a confirmed ROI marker relative to the next ROI marker.

FIGS. 9, 10, 11, and 12 show another ROI setting processing. It is possible to selectively use the above ROI setting procedure and another ROI setting procedure under the control of the control processor 31 based on a selection instruction from the operator.

Figure 9:
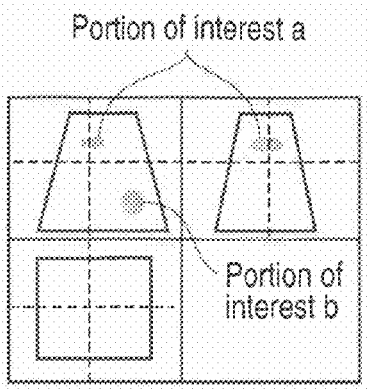
FIG. 9 is a view showing an initial window displayed on a monitor in FIG. 1 in a modification.
Figure 10:
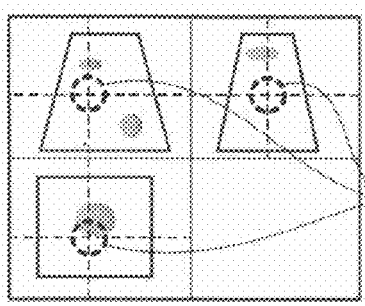
FIG. 10 is a view showing the first ROI markers and section lines in the modification.
Figure 11:
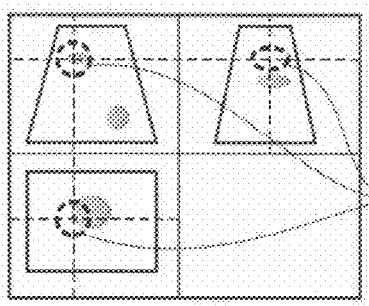
FIG. 11 is a view showing the moved first ROI markers and section lines in the modification.
Figure 12:
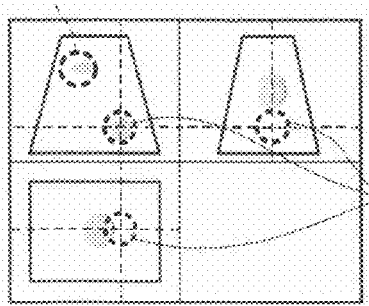
FIG. 12 is a view showing the confirmed first and second ROI markers in the modification.

As shown in FIG. 9, portions of interest a and b exist in a state in which a three-dimensional ultrasonic image can be recognized from three slice images. When the operator starts setting regions of interest, ROI markers (the first ROI markers) are superimposed on three slice images. The operator moves the first ROI marker or the intersection point on each slice image so as to position the portion of interest a in the first ROI marker. The control processor 31 performs control to always match the center of an ROI marker with an intersection point. As shown in FIG. 11, the control processor 31 also changes the size of the first ROI marker in accordance with the size of the portion of interest a. After the operator confirms a region of interest, the control processor 31 shifts to the setting of the next region of interest. As shown in FIG. 12, when the second ROI marker is superimposed on a slice image to set a region of interest in the portion of interest b, the confirmed first ROI marker is composited on the portion of interest a and is moved together with the movement of the slice image. The operator moves the second ROI marker or the intersection point on each slice image to position the portion of interest b in the second ROI marker. The control processor 31 performs control to always match the center of the second ROI marker with the intersection point.

In this case, unlike the above case, it is possible to move an ROI marker to an arbitrary position within the display area. It is also possible to set section lines which set the position of each slice image at arbitrary position within the display area, together with an ROI marker. The operator can display three proper slice images while moving section lines. The operator can arbitrarily move the ROI markers on three slice images. As in the above case, since a confirmed ROI marker is displayed while being composited with a slice image, it is possible to always refer to the ROI marker for the setting of the next ROI. This makes it possible to reduce the load of the operation of aligning a plurality of ROI markers with a plurality of portions of interest in a three-dimensional ultrasonic image.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:
1. A medical image display apparatus comprising:
an ultrasonic probe configured to generate ultrasonic waves to impinge onto a three dimensional region of an object with the ultrasonic waves, and to receive reflected ultrasonic waves from the three dimensional region of the object;
a control processor configured to generate data of a three dimensional image based on the reflected ultrasonic waves from the ultrasonic probe;
a memory configured to store data of the three dimensional image;
the control processor further configured to generate three slice images associated with three slices from the three dimensional image;
a display configured to display the three slice images respectively in three display areas;

the control processor further configured to generate three
ROI (region of interest) markers to be respectively
superimposed on the displayed three slice images, the
three ROI markers corresponding to a single ROI;
the control processor further configured to perform operation of changing relative positions between the three
slice images and the three ROI markers; and
the control processor further configured to move the three
slice images in the three display areas in accordance
with the operation of changing the relative positions
and fix the three ROI markers at center positions of the
three display areas;
wherein the control processor is further configured to
generate a confirmed ROI marker, based on an input
from an operator, representing a confirmation that the
ROI markers includes the ROI, to fix the confirmed
ROI marker relative to the slice image, and to move the
confirmed ROI marker in the display area together with
the slice image.

2. The apparatus according to claim 1, wherein the control processor is further configured to display the confirmed ROI marker separately from the slice image, and to display the confirmed ROI marker at a position fixed relative to a next ROI marker.

3. The apparatus according to claim 1, wherein the control processor is configured to superimpose two section lines corresponding to two remaining slice images for each of the three slice images.

4. The apparatus according to claim 3, wherein the two section lines intersect at a center position of each of the display areas.

5. The apparatus according to claim 3, wherein the two section lines intersect at a position of each of the ROI markers.

6. A medical image display apparatus comprising:
an ultrasonic probe configured to generate ultrasonic waves to impinge onto a three dimensional region of an object with the ultrasonic waves, and to receive reflected ultrasonic waves from the three dimensional region of the object;
a control processor configured to generate data of a three dimensional image based on the reflected ultrasonic waves from the ultrasonic probe;
a memory configured to store data of the three dimensional image;
the control processor further configured to generate three slice images associated with three slices from the three dimensional image;
a display configured to display the three slice images respectively in three display areas;
the control processor further configured to generate three ROI (region of interest) markers to be respectively superimposed on the displayed three slice images, the three ROI markers corresponding to a single ROI;
the control processor further configured to perform operation of changing relative positions between the three slice images and the three ROI markers; and
the control processor further configured to move the three ROI markers in the three display areas in accordance with the operation of changing the relative positions and fix the three slice images in the three display areas;
wherein the control processor is further configured to generate a confirmed ROI marker, based on an input from an operator, representing a confirmation that the ROI markers includes the ROI, to fix the confirmed ROI marker relative to the slice image, and to move the confirmed ROI marker in the display area together with the slice image.

7. The apparatus according to claim 6, wherein the control processor is further configured to display the confirmed ROI marker separately from the slice image, and to display the confirmed ROI marker at a position fixed relative to a next ROI marker.

8. The apparatus according to claim 6, wherein the control processor is configured to superimpose two section lines corresponding to two remaining slice images for each of the three slice images.

9. The apparatus according to claim 8, wherein the two section lines intersect at a center position of each of the display areas.

10. The apparatus according to claim 8, wherein the two section lines intersect at a position of each of the ROI markers.

11. A medical image display apparatus comprising:
an ultrasonic probe configured to generate ultrasonic waves to impinge onto a three dimensional region of an object with the ultrasonic waves, and to receive reflected ultrasonic waves from the three dimensional region of the object;
a control processor configured to generate data of a three dimensional image based on the reflected ultrasonic waves from the ultrasonic probe;
a memory configured to store data of the three dimensional image, the ultrasonic probe generating ultrasonic waves to impinge onto a three dimensional region of an object with the ultrasonic waves and receiving reflected ultrasonic waves from the three dimensional region of the object;
the control processor further configured to generate three slice images associated with three slices the three dimensional image;
a display configured to display the three slice images respectively in three display areas;
the control processor further configured to generate three ROI (region of interest) markers to be respectively superimposed on the displayed three slice images, the three ROI markers corresponding to a single ROI;
the control processor further configured to perform operation of changing relative positions between the three slice images and the three ROI markers; and
the control processor further configured to select one of a first procedure of moving the three slice images in the three display areas in accordance with operation of changing the relative position and fixing the three ROI markers at center positions of the three display areas and a second procedure of moving the three ROI markers in the three display areas in accordance with operation of changing the relative position and fixing the three slice images in the three display areas, in accordance with an instruction from an operator;
wherein the control processor is further configured to generate a confirmed ROI marker, based on an input from an operator, representing a confirmation that the ROI markers includes the ROI, to fix the confirmed ROI marker relative to the slice image, and to move the confirmed ROI marker in the display area together with the slice image.

12. An ultrasonic diagnosis apparatus comprising:
an ultrasonic probe configured to generate ultrasonic waves to impinge onto a three dimensional region of an object with the ultrasonic waves, and to receive reflected ultrasonic waves from the three dimensional region of the object;

a control processor configured to generate data of a three dimensional image based on the reflected ultrasonic waves from the ultrasonic probe;

a memory configured to store data of the three dimensional image;

the control processor further configured to generate three slice images associated with three slices from a three dimensional ultrasonic image;

a display configured to display the three slice images respectively in three display areas;

the control processor further configured to generate three ROI (region of interest) markers respectively superimposed on the three displayed slice images, the three ROI markers corresponding to a signal ROI;

the control processor further configured to change relative positions between the three slice images and the three ROI markers; and the control processor further configured to move the three slice images in the three display areas in accordance with the operation of changing the relative positions and fix the three ROI markers at center positions of the three display areas;

wherein the control processor is further configured to generate a confirmed ROI marker, based on an input from an operator, representing a confirmation that the ROI markers includes the ROI, to fix the confirmed ROI marker relative to the slice image, and to move the confirmed ROI marker in the display area together with the slice image.

13. An ultrasonic diagnosis apparatus comprising:

an ultrasonic probe configured to generate ultrasonic waves to impinge onto a three dimensional region of an object with the ultrasonic waves, and to receive reflected ultrasonic waves from the three dimensional region of the object;

a control processor configured to generate data of a three dimensional image based on the reflected ultrasonic waves from the ultrasonic probe;

a memory to store data of the three dimensional image;

the control processor further configured to generate three slice images associated with three slices from a three dimensional ultrasonic image;

a display configured to display the three slice images respectively in three display areas;

the control processor further configured to generate three ROI (region of interest) markers respectively superimposed on the three displayed slice images, the three ROI markers corresponding to a signal ROI;

the control processor further configured to change relative positions between the three slice images and the three ROI markers; and the control processor further configured to move the three ROI markers in the three display areas in accordance with the operation of changing the relative positions and fix the three slice images in the three display areas;

wherein the control processor is further configured to generate a confirmed ROI marker, based on an input from an operator, representing a confirmation that the ROI markers includes the ROI, to fix the confirmed ROI marker relative to the slice image, and to move the confirmed ROI marker in the display area together with the slice image.

14. An ultrasonic diagnosis apparatus comprising:

an ultrasonic probe configured to generate ultrasonic waves to impinge onto a three dimensional region of an object with the ultrasonic waves, and to receive reflected ultrasonic waves from the three dimensional region of the object;

a control processor configured to generate data of a three dimensional image based on the reflected ultrasonic waves from the ultrasonic probe;

a memory configured to store the data of the three dimensional image;

the control processor further configured to generate three slice images associated with three slices the three dimensional image;

a display configured to display the three slice images respectively in three display areas;

the control processor further configured to generate three ROI (region of interest) markers to be respectively superimposed on the displayed three slice images, the three ROI markers corresponding to a single ROI;

the control processor further configured to perform operation of changing relative positions between the three slice images and the three ROI markers; and the control processor further configured to select one of a first procedure of moving the three slice images in the three display areas in accordance with operation of changing the relative position and fixing the three ROI markers at center positions of the three display areas and a second procedure of moving the three ROI markers in the three display areas in accordance with operation of changing the relative position and fixing the three slice images in the three display areas, in accordance with an instruction from an operator;

wherein the control processor is further configured to generate a confirmed ROI marker, based on an input from an operator, representing a confirmation that the ROI markers includes the ROI, to fix the confirmed ROI marker relative to the slice image, and to move the confirmed ROI marker in the display area together with the slice image.

* * * * *